US006885891B2

United States Patent
Cho et al.

(10) Patent No.: US 6,885,891 B2
(45) Date of Patent: Apr. 26, 2005

(54) AUTOMATIC RATE RESPONSE SENSOR MODE SWITCH

(75) Inventors: Yong Kyun Cho, Maple Grove, MN (US); Catherine R. Condie, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 460 days.

(21) Appl. No.: 10/040,120

(22) Filed: Dec. 31, 2001

(65) Prior Publication Data

US 2003/0125778 A1 Jul. 3, 2003

(51) Int. Cl.$^7$ ............................................. A61N 1/365
(52) U.S. Cl. ........................................ 607/18; 607/27
(58) Field of Search ................... 600/481, 483, 600/506, 508, 509, 513, 522, 528, 301, 547; 607/17–19, 27, 23, 28, 63, 2

(56) References Cited

U.S. PATENT DOCUMENTS

| | | | | |
|---|---|---|---|---|
| 4,476,868 A | | 10/1984 | Thompson | 128/419 |
| 4,485,813 A | | 12/1984 | Anderson et al. | 128/675 |
| 4,527,568 A | * | 7/1985 | Rickards | 607/25 |
| 5,003,975 A | * | 4/1991 | Hafelfinger et al. | 607/28 |
| 5,052,388 A | | 10/1991 | Sivula et al. | 128/419 |
| 5,065,759 A | * | 11/1991 | Begemann et al. | 607/18 |
| 5,184,614 A | * | 2/1993 | Collins et al. | 607/107 |
| 5,201,865 A | * | 4/1993 | Kuehn | 607/8 |
| 5,224,475 A | * | 7/1993 | Berg et al. | 607/8 |
| 5,376,106 A | * | 12/1994 | Stahmann et al. | 607/18 |
| 5,387,229 A | * | 2/1995 | Poore | 607/18 |
| 5,476,483 A | | 12/1995 | Bornzin et al. | 607/17 |
| 5,476,485 A | * | 12/1995 | Weinberg et al. | 607/28 |
| 5,562,711 A | | 10/1996 | Yerich et al. | 607/17 |
| 5,607,455 A | * | 3/1997 | Armstrong | 607/8 |
| 5,626,622 A | | 5/1997 | Cooper | 607/18 |
| 5,707,398 A | * | 1/1998 | Lu | 607/27 |
| 5,722,996 A | | 3/1998 | Bonnet et al. | |
| 5,766,228 A | | 6/1998 | Bonnet et al. | |
| 5,957,861 A | | 9/1999 | Combs et al. | 600/547 |
| 6,273,856 B1 | | 8/2001 | Sun et al. | 600/300 |

* cited by examiner

*Primary Examiner*—Kennedy Schaetzle
(74) *Attorney, Agent, or Firm*—Girma Wolde-Michael; Paul H. McDowall

(57) ABSTRACT

An automatic rate response sensor mode switch is implemented in an implantable medical device to monitor and isolate any sensor in an integrated sensor scheme. The isolated sensor is based on identification of problems associated with the sensor. The implantable medical device will switch to operate with the remainder sensor(s). Specifically, an algorithm tests and determines sensor status to initiate and operate the sensor mode switch. The software continuously monitors, isolates or qualifies a sensor to come back on-line automatically.

25 Claims, 6 Drawing Sheets

SENSOR MODE SWITCH: FROM ACTIVITY ONLY MODE

AUTOMATIC RATE RESPONSE SENSOR MODE SWITCH

FIELD OF THE INVENTION

The present invention generally relates to cardiac pacemakers, and more particularly, pertains to multi-sensor, rate responsive cardiac pacemakers that vary their pacing rate by measuring a plurality of physiologic and metabolic parameters.

BACKGROUND OF THE INVENTION

Early cardiac pacemakers provided a fixed-rate implantable pulse generator (IPG) whose output could be reset by sensed atrial and/or ventricular depolarizations. Modern pacemakers can be programmed to operate in single or dual chamber modes of operation. They change their pacing rate by delivering pacing stimuli to the atrium and/or ventricle at rates that vary between an upper rate and lower rate limit by tracking the sinus or sensor-indicated rate (SIR).

More recently, single and dual chamber pacemakers have been developed which measure and change their pacing rates in response to a much wider variety of sensors that are directly or indirectly related to metabolic requirements. Such sensors include, among others, QT interval evoked response, physical activity, the change of right ventricular blood pressure over time, venous blood temperature, venous blood oxygen saturation, respiration rate, minute ventilation, and various pre and post-systolic time intervals measured by impedance or pressure sensing within the right ventricle of the heart. These sensors may be used alone or in combination with another sensor(s). Such sensor-driven pacemakers have been developed for the purpose of restoring rate response in patients lacking the ability to increase their cardiac rate adequately during exertion.

One popular method for measuring a patient's demand for oxygenated blood is to monitor the patient's level of physical activity by means of a piezoelectric, microphone-like transducer. A pacemaker which employs such a method is disclosed in U.S. Pat. No. 4,485,813 to Anderson et al. In typical prior art rate-responsive pacemakers, the pacing rate is determined according to the output from an activity sensor.

The cardiac rate, however, is normally controlled by a complex set of inputs to the autonomic nervous system. Consequently, no single sensor has been found to be entirely satisfactory for controlling rate response functions. Some of the shortcomings of single-sensor, rate responsive pacemakers, for example, include: (1) long-term sensor instability, resulting from degradation; (2) long-term changes in correlation between sensor output and how it is measured, due to physiologic changes in the patient, such as biologic/sensor interface changes due to tissue changes; (3) changes in sensor sensitivity; and (4) the need for frequent re-programming to accommodate the foregoing problems, as they are encountered.

To address these problems in single sensor of the prior art, it has been proposed to utilize other physiologically based parameters to assess a patient's metabolic demand. One such parameter is minute ventilation that has been clinically demonstrated to be a parameter that correlates directly to the actual metabolic and physiologic needs of patients and has been combined with activity sensors (piezo-electric or accelerometer) in a single pacemaker.

Thus, there are now several multiple-sensor pacemakers capable of varying their rate from multiple sensor inputs. Unfortunately, a highly reliable and efficient implementation of such multiple sensor-driven rate response has proven to be difficult and, at times, not very satisfactory. In addition to those problems listed above as to single-sensor pacemakers, other problems which are typically encountered include: (1) differences between sensors in long-term stability; (2) differences between sensors in immunity to noise; (3) differences in response time due to changing metabolic conditions; (4) differences in correlating each sensor output and measuring its output; (5) time response lags during rate response optimization process; and (6) complex setup procedures, including the need for frequent re-programming.

Various methods to overcome these multi-sensor issues have been proposed. Typically, these proposals seek to calibrate the sensor input post implant when the patient is at rest or asleep. Many sensors can be used to indicate when the patient is at rest and/or in a sleep state; such sensor signals include the activity level, the activity variance, and possibly the inclination of the patient. See, for example, U.S. Pat. No. 5,626,622, issued to Cooper, entitled "Dual Sensor Rate-Responsive Pacemaker", which discusses the use of an activity sensor to determine the activity level of the patient. See also, for example, U.S. Pat. No. 5,476,483, to Bornzin et al., entitled "System and Method for Modulating the Base Rate During Sleep for a Rate-responsive Cardiac Pacemaker", which discusses the use of activity variance to determine if the patient is at rest or sleeping.

Physician intervention during follow-up has also been asserted as a solution. The process of initialization or recalibrating a physiologic sensor post implant involves having the physician program the cardiac pacemaker so that the sensor is appropriately tuned or optimized to allow the cardiac pacemaker to accurately respond to changes in the patient's metabolic demand. The algorithms used to control physiologic sensors typically have relatively long time constants of up to 30 minutes or more. A lengthy time constant is not desirable, however, in that it consumes a substantial amount of clinical time in order to achieve the initialization or recalibration. As will be appreciated, this is also costly and undesirable in that it effectively limits the number of patients whose pacemakers may be initialized within a given period of time so as to negatively impact the efficiency of the clinical operations. Invariably, physicians end up bypassing the lengthy automatic initialization process by manually setting the response slope of the sensors. Manual optimization of the sensors is not the best approach because it is typically based on "best guess" approximation that is often highly subjective and more likely to result in non-optimal sensor rate settings.

Still further drawbacks exist with regard to the algorithms employed to optimize both the physiologic and activity sensors. These algorithms, typically referred to as "automatic slope algorithms," are used to adapt a sensor response based on a feedback mechanism. One common feedback mechanism is dependent upon whether the pacing rate achieves a maximum sensor rate (MSR) within a predetermined time period. MSR is defined as the maximum pacing rate allowed as a result of sensor control input that typically programmed from 100 to 180 pulses per minute (ppm) in 5 or 10-ppm increments. Another common feedback mechanism is dependent upon whether the pacing rate achieves a target sensor rate (TSR) that is lower than the MSR within a predetermined time period such as 8 days. Algorithms of the first type are known to result in inappropriate response optimization in that it assumes that the patient exercises up to the programmed MSR in every time period. Algorithms of the second type require programming of a patient individual TSR which can be described as the typical maximum daily achieved rate. However, this is an arbitrary rate since the physician will typically rely on subjective patient data to program the rate. Furthermore, both types of algorithms have very long time constants for optimization, typically measured in weeks or months. Such an approach is generally disclosed in U.S. Pat. No. 6,273,856 issued to Sun, et al. This process is contrary to the physician's goal of sending the patient home with an optimized response immediately after implant. Another disadvantage with these algorithms is that they typically result in extremely aggressive sensor response after a period of sedentary behavior or immobility.

An ambulatory solution to these issues has been implemented in many multi-sensor pacemakers, known as sensor cross check. Sensor cross check evaluates the input of the respective sensor and determines whether it is valid and, based on this evaluation, whether it should be used or ignored. For example, a patient with pulmonary dysfunction may be breathing somewhat rapidly and/or deeply. This breathing pattern would trigger the MV sensor to increase the rate, although the activity sensor would indicate the patient is at rest. Generally, a multi-sensor pacemaker will allow a limited increase in the pacing rate that may or may not be appropriate for this particular patient. On the other hand, if a patient is riding in a car over a bumpy road, the activity sensor might call for an increase in rate, the MV sensor would prevent any increase because it would indicate the patient is a rest. In the main, however, sensor cross checks do not provide a sensor mode switch to relieve patient symptoms caused by any inappropriate sensor responses.

A need therefore exists for an improved multi-sensor cardiac pacemaker that will automatically select the appropriate rate response sensor mode (integrated, MV only, Activity only, QT only, etc.) so as to optimize the device's performance and the patient's cardiac rate.

SUMMARY OF THE INVENTION

The present invention discloses a sensor mode switch to optimize rate responsive therapy for patients who become symptomatic with a "fixed" dual sensor mode. Symptoms may arise in a "fixed" dual sensor mode due to erroneous sensor outputs or false positives and algorithmic limitations, among others. Physicians currently interview such patients in an attempt to determine the source of the symptoms. Physicians also consult the pacemaker's diagnostics via the programmer. Then, during a follow up session, the physicians will manually "turn off" one sensor or another via the programmer. Such intervention may or may not provide the appropriate solution. Symptoms may return completely or intermittently because the incorrect sensor was "turned off."

To resolve such problems, the present invention proposes a means to identify which sensor or sensors in a dual integrated sensor mode is most probably the cause of such symptoms. The identification of the problematic sensor occurs, not in the physician's office, but rather between follow-up sessions, while the patient goes about his normal activities. Upon identification of the problematic sensor(s), the pacemaker will automatically switch from the integrated sensor mode, on a temporary or permanent basis, to a single sensor mode or, if both sensors are involved, to a non-rate-responsive mode. While the preferred embodiment will be described by using an accelerometer and minute ventilation (MV) integrated sensor, the implementation may be easily applied to or adapted with other sensor combinations, QT, pressure sensors, among others.

In the preferred embodiment, the algorithm periodically, at a fixed or programmed elapsed time basis, tests and determines sensor status. Upon detection of a problematic sensor(s), a sensor mode switch is "permanent", that is, the mode switch will remain in effect until the next follow-up session at which time the physician can intervene to reset the algorithm, if desired.

In yet another embodiment, the algorithm enables a sensor mode switch on a temporary basis upon detecting a problematic sensor. After switching, the sensor(s) continues to be evaluated periodically. If or when the problem is resolved, the algorithm will enable a sensor mode switch to the dual sensor, activity only, or MV only mode.

In another embodiment, the pacemaker patient will be given a patient feedback device that, when activated by the patient, will enable the algorithm to begin sensor evaluation (s). This feedback device may be symptom-related, that is, it will be equipped with buttons that describe potential symptoms so as to be easily understood by the patient. For example, a "racing heart" button might be pressed if or when the patient experiences too fast a heart rate when driving in a vehicle over a bumpy road. In such a case, the algorithm would evaluate the accelerometer signal and, if the signal was too frequent, switch the mode from dual sensor or activity only to the MV only mode on a temporary basis.

In a further embodiment, the patient may use the activator to switch to another sensor that is more suitable for the activity the patient wishes to pursue. For example, if the patient wishes to exercise on a stationary bike, he might switch beforehand to the MV sensor from the dual sensor or accelerometer mode because the MV signal is more suitable to this type of exercise.

All of the above embodiments will minimize physician intervention and provide substantially immediate alleviation of patient symptoms.

DETAILED DESCRIPTION OF THE DRAWINGS

Figure 1:
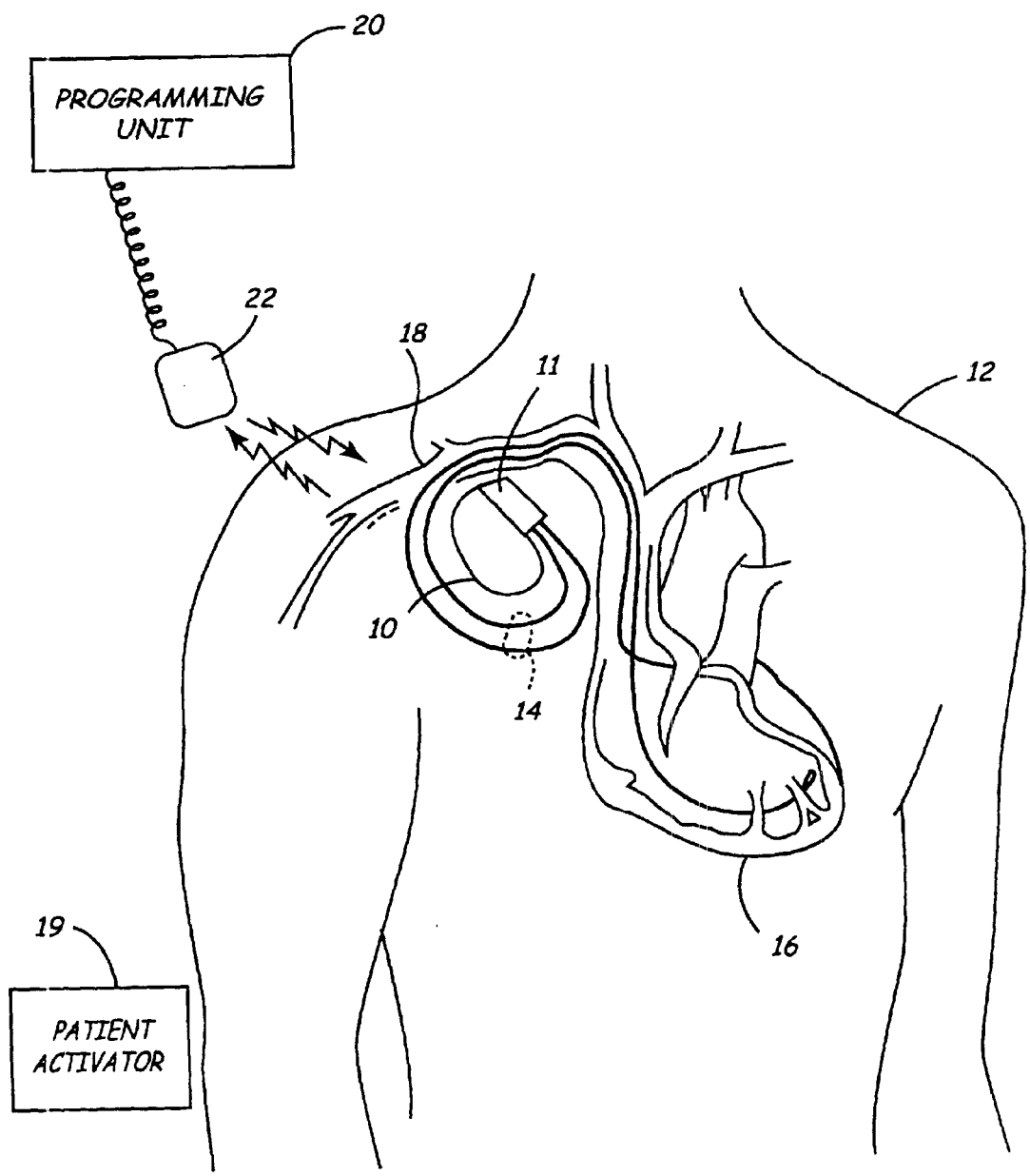
FIG. 1 is an illustration of a body-implantable device system in accordance with the present invention, including a hermetically sealed device implanted in a patient and an external programming unit.

FIG. 1 is an illustration of an implantable medical device system adapted for use in accordance with the present invention. The medical device system shown in FIG. 1 includes an implantable device 10—a pacemaker for illustration purposes—that has been implanted in a patient 12. In accordance with conventional practice in the art, pacemaker 10 is housed within a hermetically sealed, biologically inert outer casing, which may itself be conductive so as to serve as an indifferent electrode in the pacemaker's pacing/sensing circuit. One or more pacemaker leads, collectively identified with reference numeral 14 in FIG. 1 are electrically coupled to pacemaker 10 in a conventional manner and extend into the patient's heart 16 via a vein 18. The leads used may also be disposed on the external surface of the heart (not shown). Such leads are termed epicardial leads and are known to those skilled in the heart.

Disposed generally near the distal end of leads 14 are one or more exposed conductive electrodes for receiving electrical cardiac signals and/or for delivering electrical pacing stimuli to heart 16. As will be appreciated by those of ordinary skill in the art, leads 14 may be implanted with their distal end(s) situated in the atrium and/or ventricle of heart 16, in positions commonly known to those skilled in the state of the art such as, the apex of the right ventricle, atrial appendage, coronary sinus, among others.

Although the present invention will be described herein in an embodiment which includes a pacemaker, those of ordinary skill in the art having the benefit of the present disclosure will appreciate that the present invention may be advantageously practiced in connection with numerous other types of IMD systems, and indeed in any application in which it is desirable to provide a method to determine atrial thresholds in a dual chamber IMD.

Also depicted in FIG. 1 is an external programming unit 20 for non-invasive communication with implanted device 10 via uplink and downlink communication channels. Associated with programming unit 20 is a programming head 22, in accordance with conventional medical device programming systems, for facilitating two-way communication between implanted device 10 and programmer 20. In many known implantable device systems, a programming head such as that depicted in FIG. 1 is positioned on the patient's body over the implant site of the device (usually within 2-to 3-inches of skin contact), such that one or more antennae within the head can send RF signals to, and receive RF signals from, an antenna disposed within the hermetic enclosure of the implanted device or disposed within the connector block of the device, in accordance with common practice in the art. Patient 12 may communicate with IMD 10 by using patient activator 19. Patient activator 19 may be equipped with buttons that are symptom-related, e.g., too fast a heart rate, too slow a heart rate, among others. In conjunction with this embodiment or in another separate embodiment, patient activator 19 may be equipped with buttons to select one or another sensor mode.

Figure 2:
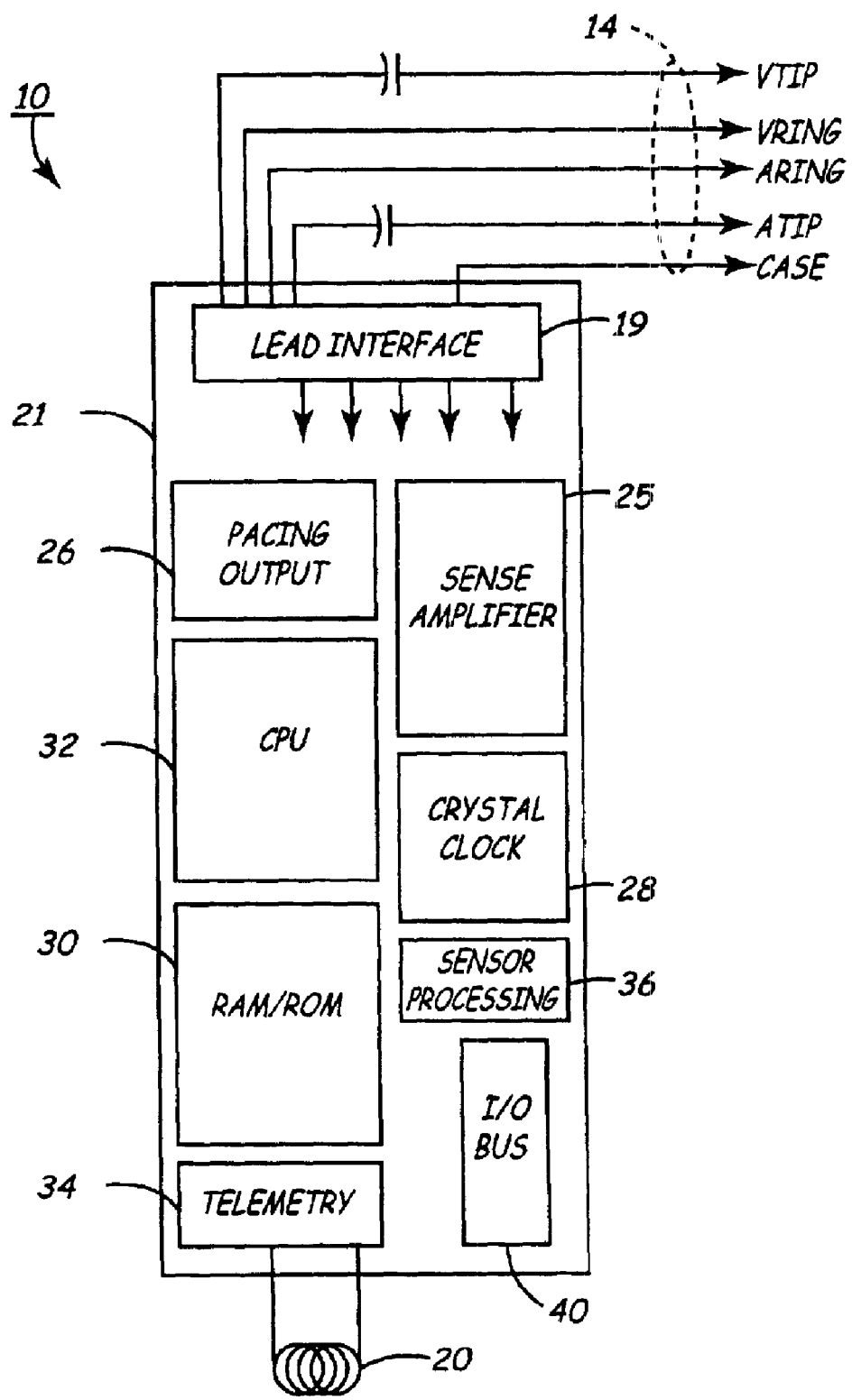
FIG. 2 is a block diagram of the implanted device from FIG. 1.

FIG. 2 is a block diagram of the electronic circuitry that typifies pulse generator 10 in accordance with the presently disclosed invention. As can be seen from FIG. 2, pacemaker 10 comprises a primary stimulation control circuit 21 for controlling the device's pacing and sensing functions. The circuitry associated with stimulation control circuit 21 may be of conventional design, in accordance, for example, with what is disclosed U.S. Pat. No. 5,052,388 issued to Sivula et al., *Method And Apparatus For Implementing Activity Sensing In A Pulse Generator*. To the extent that certain components of pulse generator 10 are conventional in their design and operation, such components will not be described herein in detail, as it is believed that design and implementation of such components would be a matter of routine to those of ordinary skill in the art. For example, stimulation control circuit 21 in FIG. 2 includes sense amplifier circuitry 25, stimulating pulse output circuitry 26, a crystal clock 28, a random-access memory and read-only memory (RAM/ROM) unit 30, and a central processing unit (CPU) 32, all of which are well-known in the art.

Pacemaker 10 also includes internal communication circuit 34 so that it is capable of communicating with external programmer/control unit 20.

With continued reference to FIG. 2, pulse generator 10 is coupled to one or more leads 14 which, when implanted, extend transvenously between the implant site of pulse generator 10 and the patient's heart 16, as previously noted with reference to FIG. 1. Physically, the connections between leads 14 and the various internal components of pulse generator 10 are facilitated by means of a conventional connector block assembly 11, shown in FIG. 1. Electrically, the coupling of the conductors of leads and internal electrical components of pulse generator 10 may be facilitated by means of a lead interface circuit 19 which functions, in a multiplexer-like manner, to selectively and dynamically establish necessary connections between various conductors in leads 14, including, for example, atrial tip and ring electrode conductors ATIP and ARING and ventricular tip and ring electrode conductors VTIP and VRING, and individual electrical components of pulse generator 10, as would be familiar to those of ordinary skill in the art. For the sake of clarity, the specific connections between leads 14 and the various components of pulse generator 10 are not shown in FIG. 2, although it will be clear to those of ordinary skill in the art that, for example, leads 14 will necessarily be coupled, either directly or indirectly, to sense amplifier circuitry 25 and stimulating pulse output circuit 26, in accordance with common practice, such that cardiac electrical signals may be conveyed to sensing circuitry 25, and such that stimulating pulses may be delivered to cardiac tissue, via leads 14. Also not shown in FIG. 2 is the protection circuitry commonly included in implanted devices to protect, for example, the sensing circuitry of the device from high voltage stimulating pulses.

As previously noted, stimulation control circuit 21 includes central processing unit 32 which may be an off-the-shelf programmable microprocessor or micro controller, but in the present invention is a custom integrated circuit. Although specific connections between CPU 32 and other components of stimulation control circuit 21 are not shown in FIG. 2, it will be apparent to those of ordinary skill in the art that CPU 32 functions to control the timed operation of stimulating pulse output circuit 26 and sense amplifier circuit 25 under control of programming stored in RAM/ROM unit 30. It is believed that those of ordinary skill in the art will be familiar with such an operative arrangement.

With continued reference to FIG. 2, crystal oscillator circuit 28, in the presently preferred embodiment a 32,768-Hz crystal controlled oscillator provides main timing clock signals to stimulation control circuit 21. Again, the lines over which such clocking signals are provided to the various timed components of pulse generator 10 (e.g., microprocessor 32) are omitted from FIG. 2 for the sake of clarity.

It is to be understood that the various components of pulse generator 10 depicted in FIG. 2 are powered by means of a battery (not shown) that is contained within the hermetic enclosure of pacemaker 10, in accordance with common practice in the art. For the sake of clarity in the Figures, the battery and the connections between it and the other components of pulse generator 10 are not shown.

Stimulating pulse output circuit 26, which functions to generate cardiac stimuli under control of signals issued by CPU 32, may be, for example, of the type disclosed in U.S. Pat. No. 4,476,868 to Thompson, entitled *Body Stimulator*

*Output Circuit*, which patent is hereby incorporated by reference herein in its entirety. Again, however, it is believed that those of ordinary skill in the art could select from among many various types of prior art pacing output circuits that would be suitable for the purposes of practicing the present invention.

Sense amplifier circuit 25, which is of conventional design, functions to receive electrical cardiac signals from leads 14 and to process such signals to derive event signals reflecting the occurrence of specific cardiac electrical events, including atrial contractions (P-waves) and ventricular contractions (R-waves). CPU provides these event-indicating signals to CPU 32 for use in controlling the synchronous stimulating operations of pulse generator 10 in accordance with common practice in the art. In addition, these event-indicating signals may be communicated, via uplink transmission, to external programming unit 20 for visual display to a physician or clinician.

Figure 3:
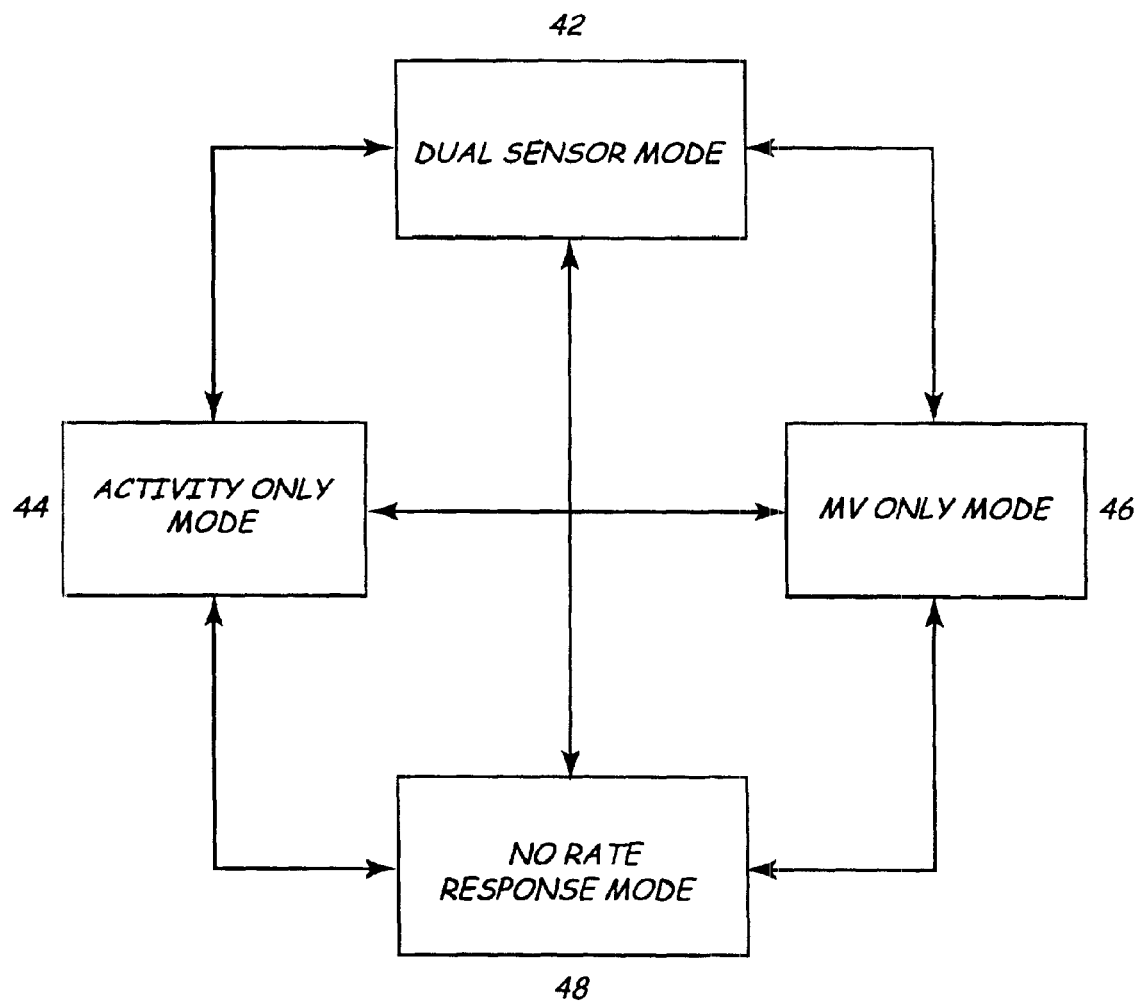
FIG. 3 is a flow diagram illustrating the overall concept of automatic sensor mode switching.

FIG. 3 is a flow diagram that provides the overall picture of the possible sensor mode switches. In a first situation, the pacemaker is programmed to dual sensor mode 42 and permanent switch (not shown) upon detecting an issue with one or both sensors. A permanent sensor mode switch means that it would stay in that mode until the next follow-up session at which time, the physician could reprogram the pacemaker to the previous mode or another as appropriate. If there is a problem with MV sensor 46, the pacemaker would automatically switch to activity only mode 44 on a permanent basis. If, however, there is a problem with both sensors 44 and 46, the pacemaker would permanently switch to non-rate-responsive mode 48.

Alternatively, when the pacemaker is programmed to a sensor mode switch on a temporary basis, other possibilities come into play. A mode switch from dual sensor mode 42 or MV only mode 46 to activity only mode 44 may be only temporary, that is, until the situation with the activity sensor 44 corrects itself, for example, riding over a bumpy road in a car. Similarly, a temporary switch to MV only mode 46 from dual sensor mode 42 or activity only mode 44 will switch back to those respective modes when the MV signal is corrected, for example, too small of a signal to activate MV sensor 46 due to shallow breathing. Similarly, rate responsive pacing may be restored to the previous mode 42, 44, or 46 from non-rate-responsive mode 48 when one or both sensor signals are corrected.

Figure 4:
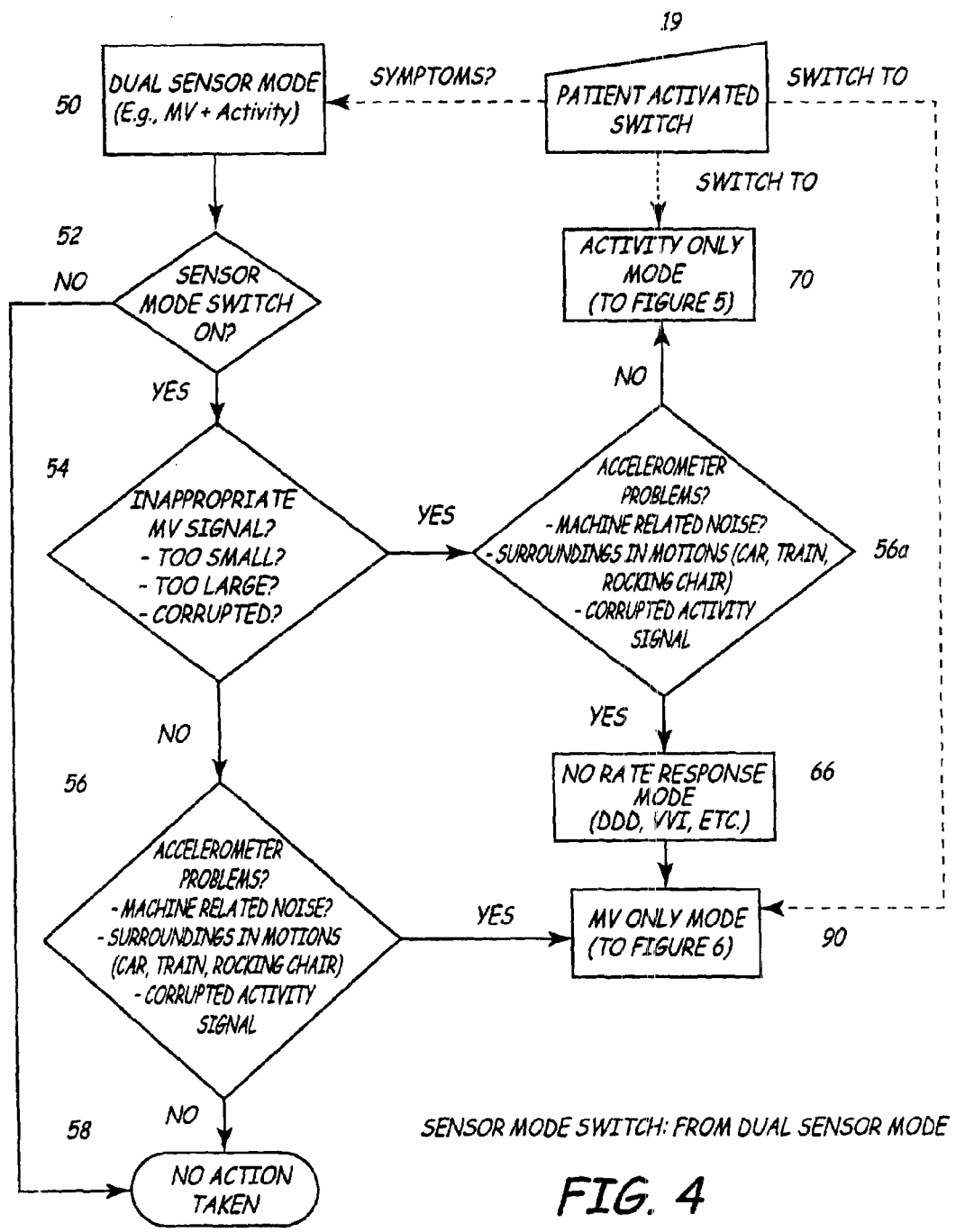
FIG. 4 is a flow diagram illustrating the circumstances under which the pacemaker would switch from the integrated dual sensor mode a single sensor mode, such as activity or MV.
Figure 5:
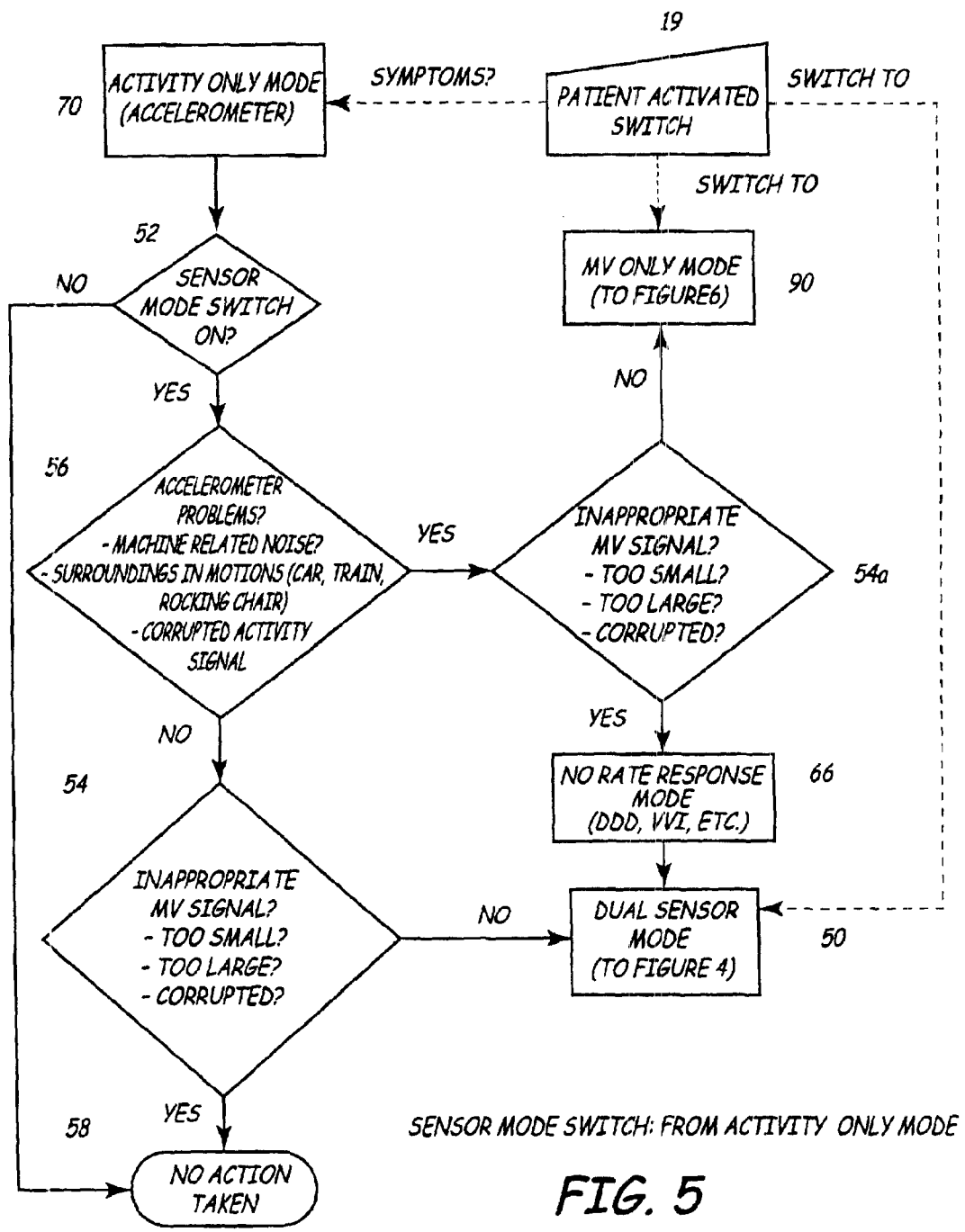
FIG. 5 is a flow diagram illustrating the circumstances under which the pacemaker would switch from the activity only mode to the MV only mode or to the integrated dual sensor mode.
Figure 6:
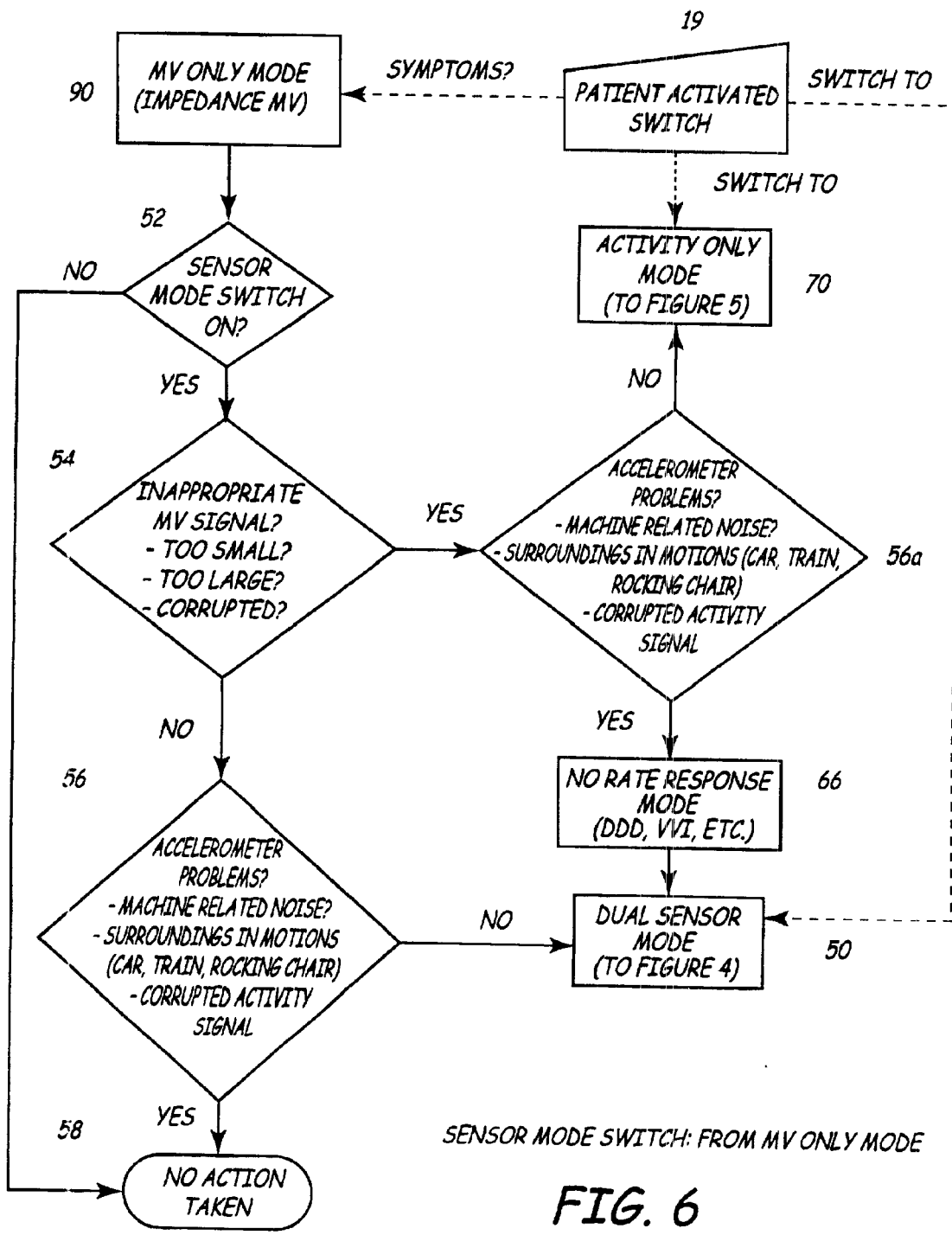
FIG. 6 is a flow diagram illustrating the circumstances under which the pacemaker would switch from the MV only mode to the activity only mode or to the integrated dual sensor mode.

Referring now to FIGS. 4, 5 and 6 sensor mode switch may be initiated from any sensor mode Dual 50 (FIG. 4), Activity only 70 (FIG. 5), or MV only 90 (FIG. 6). With reference to FIG. 4, when sensor mode switch 52 is enabled, various sensor checks 54 and 56 can be applied to determine whether or if there should be a sensor mode switch 50, 70, 90 or a switch to a non-rate-responsive mode 66. If sensor mode switch 52 is disabled, no action 58 may be taken, that is, sensor checks 54 and 56 may not begin.

Inappropriate MV signal 54 include the following:

High MV signal, that is, an inappropriately high/large transthoracic impedance signal without a corroborating activity signal. These high MV signals may be of a physiologic origin such as pulmonary edema (as described and disclosed in U.S. Pat. No 5,957,861 issued to Combs, et al), Cheyne-Stokes respiration, central or obstructive sleep apnea, hyperventilation, and coughing among others.

Low MV signal, that is, an inappropriately low/small transthoracic impedance signal. These very low counts may be due to hardware problems. Somewhat incongruously, very high respiration rates (e.g., greater than 60 breathes per minute) that may result from swimming can also cause low MV counts.

Noisy MV signal, that is, non-physiological transthoracic impedance signal originated by upper body movement, such as those coming from arm movement and shoulder rotation, among others.

Lead problems, that is, from a dislodged, fractured, or incorrect lead type (epicardial, bi-atrial, etc.), among others.

Low Delta MV (DMV), that is, a low DMV caused by an extended time of exercise that leads to an overly high long-term average (LTA). A potential method of detecting this condition may include comparison with setpoints, as disclosed in U.S. Pat. No. 5,562,711 issued to Yerich, et al. For example, the algorithm might compare the percentage of setpoints required to reach the Activity of Daily Living (ADL) rate vis-à-vis the percentage of setpoints required to reach the upper rate. Too high an LTA may be due to an exercise period of long duration (>1 hour), such a might occur with a marathon runner. Other causes include a night of restless sleep, bradycardia with a heart rate <48 bpm, a noisy or corrupted MV signal, among others.

Accelerometer problems 56 include the following:

Non-physiologic accelerometer signal, such a may occur when riding in a car or train, or on a horse, using a rocking chair, using a jack hammer, among others.

Low accelerometer signal, that is, the sensor counts that cross the activity threshold are substantially lower than the setpoints stemming from the transthoracic impedance signals. Such can be the case from riding a road bike on a smooth surface, exercising on a stationary bike, or using a wheel chair. The low counts may stem from a hardware problem or the activity threshold being set too high.

High number of activity counts without MV corroboration, such as may occur due to an exercise period of long duration (>1 hour).

Patient activated switch 19 may be used by the patient to initiate sensor(s) check upon experiencing symptoms or, alternatively, to switch from the active sensor(s) to another sensor. As indicated above, this switch to another sensor may be initiated prior to engaging in an activity for which another sensor is more appropriate.

Turning now to FIG. 4, when the pacemaker is in dual sensor mode 50, and sensor mode switch 52 is on, the algorithm will first check the appropriateness of the MV signal 54. If there are no problems with the MV signal, the algorithm will turn to checking the activity signal 56. If no problem exists with the accelerometer, no action is taken 58.

Returning to 54 during which time a problem is found with the MV signal, as described above, the algorithm switches its attention to the activity/accelerometer 56a and conducts a test on this sensor. If there are no issues with this sensor an immediate switch to activity only mode 70 takes place. On the other hand, if check of accelerometer also fails, there is an immediate switch to non-rate-responsive mode 66.

Returning to accelerometer problems 56, any issue with the accelerometer would result in an immediate switch to MV only mode 90.

FIG. 5 delineates the sequence of checks and sensor mode switching when the pacemaker is operating in activity only mode 70. Since the pacemaker is operating in the activity mode, the algorithm first checks the accelerometer 56 with a subsequent check of the MV signal 54. No action is taken 58, if both sensors check out correctly. On the other hand, if accelerometer check 56 is failed, the algorithm goes on to check MV sensor 54a. If this check is passed, an immediate switch to MV only 90 takes place. If the check fails, an immediate switch to a non-rate-responsive mode 50 occurs.

FIG. 6 delineates the sequence of checks and sensor mode switching when the pacemaker is operating in MV only mode 90. Since the pacemaker is operating in the MV mode, the algorithm first checks the MV sensor 54 with a subsequent check of the activity signal 56. No action is taken 58, if both sensors check out correctly. On the other hand, if MV check 54 is failed, the algorithm goes on to check activity sensor 56a. If this check is passed, an immediate switch to activity only 70 takes place. If this check fails, an immediate switch to a non-rate-responsive mode 50 occurs.

The preceding specific embodiments are illustrative of the practice of the invention. It is to be understood, therefore, that other expedients known to those of skill in the art or disclosed herein may be employed without departing from the invention or the scope of the appended claim. It is therefore to be understood that the invention may be practiced otherwise than is specifically described, without departing from the scope of the present invention. As to every element, it may be replaced by any one of infinite equivalent alternatives, only some of which are disclosed in the specification.

What is claimed is:

1. An automatic mode switch implemented in a medical device comprising:
    a plurality of integrated sensors operatively coupled to a medical device, wherein each of said plurality of integrated sensors provides a signal to the medical device usable to influence a cardiac pacing rate of the medical device and wherein said medical device comprises a dual integrated-sensor operating mode and can mode switch between operating: in a dual sensor mode, in a single sensor mode, in a non-rate-responsive sensor mode based on the signal from all, one, or none of the plurality of integrated sensors;
    means for testing said plurality of integrated sensors by comparing for a given period of time the output signals from each said sensor to other of the plurality of integrated sensors to determine if the sensors are providing physiologically consistent signals; and
    for each one of said plurality of integrated sensors that does not provide physiologically consistent signals, means for isolating each one of said plurality of integrated sensors and for switching the coupling of the sensors to the medical device so that each one of the plurality of integrated sensors is decoupled from said medical device such that the medical device operates in one of a single sensor mode and a non-rate-responsive sensor mode.

2. The mode switch of claim 1 wherein said switching remains fixed to operate with said remainder sensors until a reset of the coupling is executed either automatically or via manual selection of a telemetry command to reset is received by the medical device.

3. The mode switch of claim 1 wherein said means for isolating operates on a temporary basis and further comprises means for re-coupling said sensor to said medical device.

4. A mode switch according to claim 1, wherein said means for testing comprises:
    a comparison of an output signal from each of at least a pair of said plurality of integrated sensors;
    an impedance check of at least one of said plurality of integrated sensors;
    structure for comparing the output signals acquired during a period of known activity of the patient.

5. A mode switch according to claim 4, wherein said means for testing is invoked either manually or automatically by an electronic circuitry of said medical device.

6. A mode switch according to claim 1, wherein said medical device comprises an implantable medical device.

7. A mode switch according to claim 6, wherein said implantable medical device comprises an implantable pulse generator.

8. A mode switch according to claim 7, wherein at least one of said plurality of integrated sensors comprises: an accelerometer, a pressure sensor, an impedance sensor, an acoustic sensor, an activity sensor, a piezoelectric sensor or a heart rate sensor.

9. An automatic mode switch according to claim 6, further comprising an external, manually activated telemetry unit, wherein said telemetry unit provides a signal to the medical device and said signal operates to enable or disable the means for isolating.

10. An automatic mode switch according to claim 9, wherein the signal initiates at least one of a non-physiologic "racing heart" response and a physiologic minute ventilation (MV) response.

11. An automatic mode switch according to claim 10, wherein the non-physiologic "racing heart" response comprises one of a non-rate-responsive pacing mode and a physiologic rate-responsive minute ventilation (MV) mode.

12. A mode switch according to claim 1, wherein said means for isolating and for switching comprises a means for interrupting an electrical coupling between the sensor and the medical device.

13. A mode switch according to claim 12, wherein the means for interrupting the electrical coupling comprises providing an out-of-range signal from said sensor.

14. A computer readable medium for providing electronic signals operable to execute a method of mode switching in an implantable medical device, said medium comprising:
    instructions for interrogating a plurality of integrated sensors that are operatively coupled to a medical device, wherein each of said plurality of integrated sensors provides a signal to the medical device usable to influence a cardiac pacing rate of the medical device and wherein said medical device comprises a dual integrated-sensor operating mode and can mode switch between operating: in a dual sensor mode, in a single sensor mode, in a non-rate-responsive sensor mode based on the signal from all, one, or none of the plurality of integrated sensors;
    instructions for testing a said plurality of integrated sensors by comparing for a given period of time the output signals from each said sensor to other of the plurality of integrated sensors to determine if the sensors are providing physiologically consistent signals; and
    for each one of said plurality of integrated sensors that does not provide physiologically consistent signals, instructions for isolating each one of said plurality of integrated sensors and for switching the coupling of the sensors to the medical device so that each one of the plurality of integrated sensors is decoupled from said medical device such that the medical device operates in one of a single sensor mode and a non-rate-responsive sensor mode.

15. A medium according to claim 14 wherein said medical device comprises an implantable medical device.

16. A medium according to claim 15, wherein said implantable medical device comprises implantable pulse generator.

17. A medium according to claim 16, wherein at least one of said plurality of integrated sensors comprises: an accelerometer, a pressure sensor, an impedance sensor, an acoustic sensor, an activity sensor, a piezoelectric sensor, a heart rate sensor.

18. A method of mode switching a medical device, comprising:

operatively coupling a plurality of integrated sensors to a medical device, wherein each of said plurality of integrated sensors provides a signal to the medical device to influence a cardiac pacing rate of the medical device and wherein said medical device comprises a dual integrated-sensor operating mode and can mode switch between operating: in a dual sensor mode, in a single sensor mode, in a non-rate-responsive sensor mode based on the signal from all, one, or none of the plurality of integrated sensors;

testing a said plurality of integrated sensors by comparing for a given period of time the output signals from each said sensor to other of the plurality of integrated sensors to determine if the sensors are providing physiologically consistent signals; and for each one of said plurality of integrated sensors that does not provide physiologically consistent signals, isolating each one of said plurality of integrated sensors, and for switching the coupling of the sensors to the medical device so that each one of the plurality of integrated sensors that does not provide physiologically consistent signals is decoupled from said medical device such that the medical device operates in one of a single sensor mode and a non-rate-responsive sensor mode.

19. A method according to claim 18, wherein said switching remains fixed to operate with a remainder of the sensors until a reset of the coupling is executed either automatically or via manual selection of a telemetry command to reset is received by the medical device.

20. A method according to claim 18, wherein said isolating step occurs for a temporary period of time and further comprising re-coupling said sensor to said medical device following said temporary period of time.

21. A method according to claim 18, wherein said testing steps comprises:

comparing an output signal from each of at least a pair of said plurality of integrated sensors;

checking an impedance value of at least one of said plurality of integrated sensors; and comparing the output signals acquired during a period of known activity of a patient.

22. A method according to claim 21, wherein said testing step is invoked either manually or automatically via electronic circuitry of said medical device.

23. A method according to claim 18, wherein said medical device comprises an implantable medical device.

24. A method according to claim 23, wherein said implantable medical device comprises an implantable pulse generator.

25. A method according to claim 24, wherein at least one of said plurality of integrated sensors comprises: an accelerometer, a pressure sensor, an impedance sensor, an acoustic sensor, an activity sensor, a piezoelectric sensor, a heart rate sensor.

* * * * *